United States Patent
Minekus

(10) Patent No.: US 9,575,044 B2
(45) Date of Patent: Feb. 21, 2017

(54) METHOD, DEVICE AND COMPUTER PROGRAM PRODUCT FOR ASSESSING THE DISINTEGRATION OF A DOSAGE FORM IN THE GASTROINTESTINAL TRACT

(75) Inventor: Mans Minekus, Werkhoven (NL)

(73) Assignee: Triskelion B.V., Zeist (NL)

( * ) Notice: Subject to any disclaimer, the term of this patent is extended or adjusted under 35 U.S.C. 154(b) by 166 days.

(21) Appl. No.: 13/389,304

(22) PCT Filed: Aug. 6, 2010

(86) PCT No.: PCT/NL2010/050500
§ 371 (c)(1),
(2), (4) Date: Mar. 30, 2012

(87) PCT Pub. No.: WO2011/016726
PCT Pub. Date: Feb. 10, 2011

(65) Prior Publication Data
US 2012/0279324 A1    Nov. 8, 2012

(30) Foreign Application Priority Data

Aug. 7, 2009    (EP) .................................. 09167516

(51) Int. Cl.
*G01N 33/15*    (2006.01)
*G09B 23/30*    (2006.01)
(Continued)

(52) U.S. Cl.
CPC ............ *G01N 33/15* (2013.01); *G09B 23/12* (2013.01); *G09B 23/303* (2013.01); *G09B 23/32* (2013.01); *G01N 2013/006* (2013.01)

(58) Field of Classification Search
CPC ......... G09B 23/28; G09B 23/30; G09B 23/32; G09B 23/303; G09B 23/12; G01N 33/15; G01N 2013/006
(Continued)

(56) References Cited

U.S. PATENT DOCUMENTS 3,330,368 A * 7/1967 Baran et al. ................... 175/94
4,247,298 A * 1/1981 Rippie ........................... 436/2
(Continued)

FOREIGN PATENT DOCUMENTS

CN    101087594 A    12/2007
EP    0 642 382 B1    2/1998
(Continued)

OTHER PUBLICATIONS

"Stomach", The McGraw-Hill Companies, Inc., http://www.mhhe.com/biosci/esp/2002_general/Esp/folder_structure/ab/m4/s5/abm4s5_10.htm, accessed Aug. 7, 2004.*
(Continued)

*Primary Examiner* — Peter Macchiarolo
*Assistant Examiner* — Nathaniel Kolb
(74) *Attorney, Agent, or Firm* — Banner & Witcoff, Ltd.

(57) ABSTRACT

The invention relates to a device for assessing the disintegration of a dosage form in the gastrointestinal tract, comprising a wall surrounding a cell for being filled with a fluid and for receiving the dosage form, further comprising a pressurizable compartment arranged exterior to the wall for repeatedly deforming the wall between a first state and a second state wherein the volume of the cell in the first state is larger than in the second state, wherein the device also comprises controlling means for quantitatively controlling a fluid flow from and into the cell, and/or for quantitatively controlling a contact force that the wall exerts on the dosage form.

15 Claims, 5 Drawing Sheets

(51) Int. Cl.
*G09B 23/12* (2006.01)
*G09B 23/32* (2006.01)
*G01N 13/00* (2006.01)

(58) Field of Classification Search
USPC .................. 73/866.4; 600/593; 434/262–275
See application file for complete search history.

(56) References Cited

U.S. PATENT DOCUMENTS

| | | | | |
|---|---|---|---|---|
| 5,483,994 | A * | 1/1996 | Maurer | G01L 19/0645 138/30 |
| 5,525,305 | A * | 6/1996 | Minekus et al. | 422/111 |
| 5,827,984 | A * | 10/1998 | Sinnreich et al. | 73/866 |
| 6,022,733 | A * | 2/2000 | Tam et al. | 435/287.1 |
| 7,179,630 | B2 | 2/2007 | Lassen et al. | |
| 7,611,630 | B2 * | 11/2009 | Babcock et al. | 210/649 |
| 7,811,297 | B2 * | 10/2010 | Cox et al. | 606/151 |
| 8,043,270 | B2 | 10/2011 | Burke et al. | |
| 8,092,222 | B2 * | 1/2012 | Wickham | B01F 5/0685 434/127 |
| 8,257,085 | B2 * | 9/2012 | Alric et al. | 434/127 |
| 8,647,861 | B2 * | 2/2014 | Ingber et al. | 435/289.1 |
| 2003/0073061 | A1 | 4/2003 | Toomey | |
| 2006/0288805 | A1 * | 12/2006 | Das et al. | 73/866 |
| 2008/0206728 | A1 * | 8/2008 | Wickham | B01F 5/0685 434/272 |
| 2008/0275368 | A1 | 11/2008 | Gregersen et al. | |
| 2009/0240442 | A1 * | 9/2009 | Zeng | G01N 33/15 702/23 |
| 2010/0126287 | A1 * | 5/2010 | Burke et al. | 73/865.6 |
| 2010/0262381 | A1 * | 10/2010 | Zeng | G01N 33/15 702/23 |
| 2011/0020780 | A1 * | 1/2011 | Alric | G09B 23/32 434/272 |
| 2011/0250585 | A1 * | 10/2011 | Ingber et al. | 435/5 |

FOREIGN PATENT DOCUMENTS

| | | | |
|---|---|---|---|
| FR | 2923065 | 5/2009 | |
| FR | WO 2009087314 A1 * | 7/2009 | ............ G09B 23/32 |
| NL | 9201907 A | 6/1994 | |
| RU | 2200979 C2 | 3/2003 | |
| WO | 94/09895 | 5/1994 | |
| WO | 03/034060 A1 | 4/2003 | |
| WO | 2006052742 | 5/2006 | |
| WO | 2007010238 | 1/2007 | |
| WO | 2008/112245 A1 | 9/2008 | |
| WO | 2008/137504 A1 | 11/2008 | |
| WO | 2009087314 | 7/2009 | |
| WO | WO 2009087314 A1 * | 7/2009 | |

OTHER PUBLICATIONS

"Pyloric Sphincter", visualphotos.com, http://www.visualphotos.com/image/lx7209646/pyloric_sphincter_pill_camera_view, accessed Feb. 27, 2014.*
"Disintegration of Solid Foods in Human Stomach" by F. Kong et al. in: Journal of food science, vol. 73, Nr. 5, pp. R67-R80, 2008.
"A model Stomach System to Investigate Disintegration Kinetics of Solid Foods during Gastric Digestion" by F. Kong et al. in: Journal of food science, vol. 73, Nr. 5, pp. E202-E210, 2008.
"Comparison of the mechanical destructive force in the small intestine of dog and human" by Masaharu Kamba et al. in: International Journal of pharmaceutics, vol. 237, pp. 139-149, 2002.
"Physical tests <701> Disintegration" in: United States Pharmacopeia, 28 NF 23, pp. 2411-2412, 2005.
"Disintegration of tablets and capsules" in: European Pharmacopoeia, 01/2008:20901-01/2008:20903, Chapter 2.9.1-Chapter 2.9.3, pp. 263-275.
"Comparison of the rates of disintegration, gastric emptying, and drug absorption following administration of a new and a conventional paracetamol formulation, using gamma scintigraphy" in: Pharmaceutical Research, vol. 20, No. 10, pp. 1668-1673.

* cited by examiner

METHOD, DEVICE AND COMPUTER PROGRAM PRODUCT FOR ASSESSING THE DISINTEGRATION OF A DOSAGE FORM IN THE GASTROINTESTINAL TRACT

CROSS-REFERENCE TO RELATED APPLICATIONS

This application is a U.S. National Stage application under 35 U.S.C. §371 of International Application PCT/NL2010/050500 (published as WO 2011/016726 A1), filed Aug. 6, 2010, which claims priority to Application EP 09167516.5, filed Aug. 7, 2009. Benefit of the filing date of each of these prior applications is hereby claimed. Each of these prior applications is hereby incorporated by reference in its entirety.

The invention relates to a method for assessing the disintegration of a dosage form in the gastrointestinal tract, to a device for assessing the disintegration of a dosage form in the gastrointestinal tract and to a computer programme product for assessing the disintegration of a dosage form in the gastrointestinal tract.

Pharmaceutical compounds and nutritional supplements can be administered to the body by ingesting dosage forms, such as tablets, comprising these compounds and/or supplements. The speed and the extent of uptake in the body of these dosage form components is usually influenced by the conditions present in the different parts of the gastrointestinal tract (GI tract). In order to be able to improve the bio-availability of the components, it is important to gain knowledge of the behaviour of dosage forms in the GI tract, in particular knowledge of the disintegration of dosage forms and/or the release of the active ingredient from the dosage form.

An important method to gain such knowledge is to make use of a model wherein a dosage form is exposed to the physiological conditions that exist in the (different parts of the) gastrointestinal tract. Such physiological conditions can generally be discriminated by environmental parameters such as pH, temperature and presence/concentration of compounds (e.g. ingested material, salts, enzymes, metabolites) and by mechanical parameters such as the force, the extent, duration, speed and frequency of contraction of a wall of a part of the GI tract.

EP 0 642 382 B1 describes a model to mimic physiological conditions in the stomach and small intestine. This so-called "TNO Ingestion Model" (TIM) comprises different chambers representing the different compartments of the GI tract (e.g. the stomach, duodenum, jejunum and ileum). Each of these chambers is designed to simulate therein the respective pH, temperature, peristaltic movements, mechanical mixing, secretion of digestion enzymes, bile and pancreatic juices, and absorption of digested products with membranes.

The compartments of the model comprise glass jackets that enclose flexible membranes/sleeves wherein the chyme is present. By changing the (water) pressure in the space between the jackets and the membranes, the membranes may be compressed and relaxed, whereby the chyme is mixed and peristaltic movement may be simulated. These peristaltic movements are used to transport the chyme from one compartment to a next one. Further, the monitoring of the environmental parameters, the transport of the chyme, the secretion of the different digestion juices and the removal of digested products and water may be controlled continuously.

So far, the use of TIM has focused more on mimicking of the environmental parameters than on mimicking of mechanical parameters. Mechanical parameters in the different parts of the GI tract may play a prominent role in the disintegration of dosage forms in the GI tract. Therefore, it would be an important improvement to also incorporate realistic mechanical parameters, and thus allow to study the disintegration of dosages forms under realistic mechanical conditions for different part of the GI tract in time.

It is an objective of the present invention to provide a novel device that may serve as an alternative for a known device for assessing the disintegration of a dosage form in the GI tract. It is in particular an object of the present invention to provide a device that simulates the GI tract more properly.

More in particular, it is an objective of the present invention to provide a device that is suitable for assessing the release of components from a dosage form in the GI tract.

It is further an objective to provide a novel method for assessing the disintegration of a dosage form in the GI tract.

It has now been found possible to make use of a certain pressurizable compartment in combination with specific controlling means.

Accordingly, the invention relates to a method for assessing the disintegration of a dosage form in the gastrointestinal tract, comprising the steps of placing a dosage form in a cell surrounded by a wall;
repeatedly deforming the wall between a first state and a second state, wherein the volume of the cell in the first state is larger than in the second state, by pressurizing and depressurizing, respectively, a pressurizable compartment arranged exterior to the wall; and
quantitatively controlling a contact force that the wall exerts on the dosage form.

The invention further relates to a device for assessing the disintegration of a dosage form in the gastrointestinal tract, comprising a wall surrounding a cell for being filled with a fluid and for receiving the dosage form, further comprising a pressurizable compartment arranged exterior to the wall for repeatedly deforming the wall between a first state and a second state wherein the volume of the cell in the first state is larger than in the second state, wherein the device also comprises controlling means for quantitatively controlling a contact force that the wall exerts on the dosage form.

Deformation between the two states of the wall is accomplished by introducing a gas or a liquid into the pressurizable compartment, or by withdrawing a gas or a liquid out of the pressurizable compartment. Due to the deformation of the wall, the volume of the cell changes; the introduction of a gas or a liquid into the pressurizable compartment results in a reduction of the volume of the cell, and the sucking of a gas or a liquid out of the pressurizable compartment results in an increase of the volume of the cell. As a result of the decrease or the increase of the volume in the cell, the fluid present in the cell will be pressed out of the cell and drawn into the cell, respectively. By controlling the pressure in the pressurizable compartment the cell contracts or relaxes.

The first state and the second state are the extreme positions of the wall during a cycle of decreasing the cell volume and increasing the cell volume. Accordingly, with a cycle is meant the deformation of the wall from the first state into the second state, followed by the reverse deformation until the first state of the next cycle is reached. When performing a plurality of subsequent cycles, the first state in a subsequent cycle may be the same as that in a preceding cycle, i.e. the first states of multiple cycles may correspond to the same deformation so that multiple cycles start with the same cell volume. However, the first stage of a subsequent cycle may also be chosen differently from that of a preceding cycle. Analogously, the second stage of a subsequent cycle may also be the same as or different from the second stage in a preceding cycle. With such variations in the first stages of subsequent cycles and in the second stages of subsequent cycles, it is possible to vary the amplitude of the cell volume independently from cycle to cycle. For the purpose of the invention, the volume of the cell in the first state is larger than in the second state.

It is understood that the wall may be in a state that is intermediary between the first and the second state of a cycle, for example when the introduction or sucking of the gas or liquid is interrupted. Such operation results in a stepwise decrease and increase, respectively, of the volume of the cell.

By quantitatively controlling the amount and the flowrate of a gas or a liquid that is introduced into the pressurizable compartment and the pressure exerted on the dosage from by the wall, it has become possible to exert forces on a dosage form in a controlled manner. It has in particular become possible to exert and reproduce mechanical forces on a dosage form, and independently thereof to control fluid mechanics of the fluid surrounding the dosage form under physiological conditions that are similar to those in the GI tract.

By way of example only, embodiments of the present invention will now be described with reference to the accompanying figures in which FIG. 1 shows a schematic side view of an embodiment of a device according to the invention;

The figures are merely schematic views of preferred embodiments according to the invention. In the figures, the same reference numbers refer to equal or corresponding parts.

Figure 1:
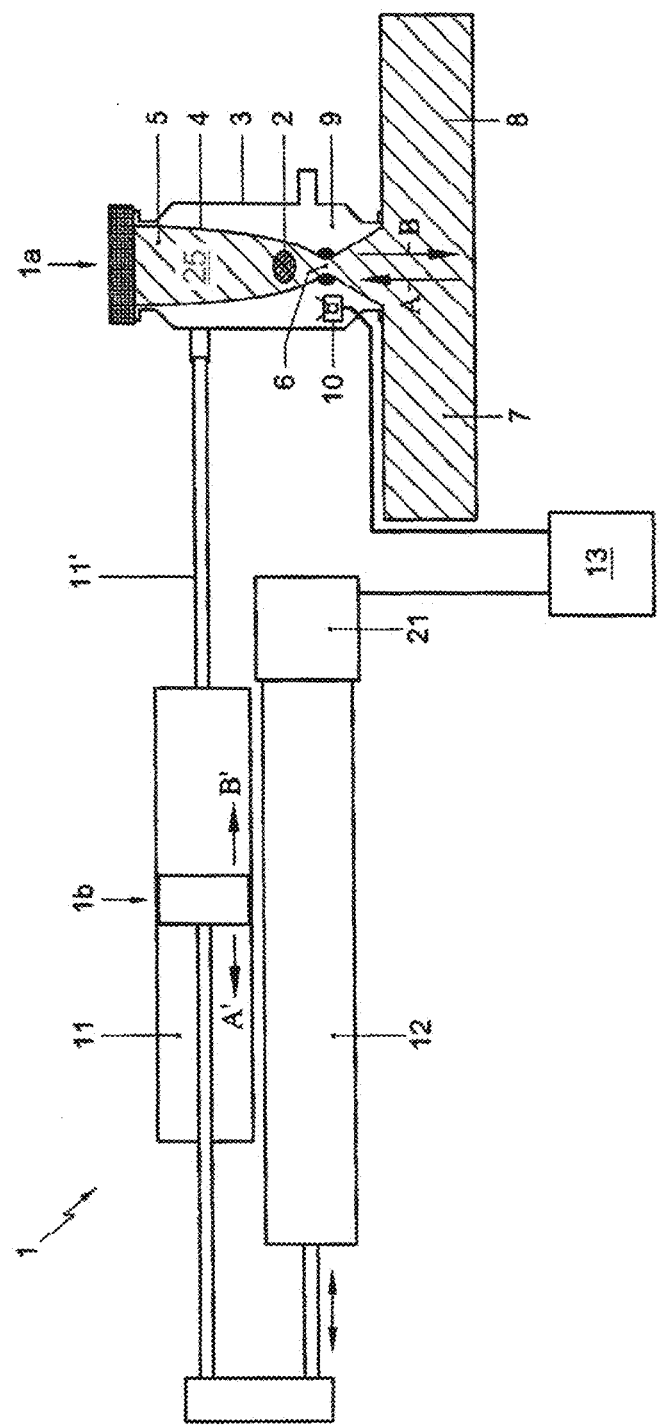

FIG. 1 shows a schematic cross sectional view of a first embodiment of a device 1 according to the invention, comprising a disintegration unit 1a and a controlling means 1b. The device 1 is arranged for assessing the disintegration of a dosage form 2 in the GI tract. Thereto, the disintegration unit 1a comprises a chamber 3 having a rigid outer wall and a flexible inner wall 4. Alternatives exist for chamber 3, for example a tyre having merely flexible wall sections. The flexible wall 4 of the chamber 3 defines a cell 5 that is surrounded by the flexible wall 4. During operation, the cell 5 comprises the dosage form 2 to be assessed for its disintegration. In particular, the wall 4 forms a pocket 25 mainly enclosing the cell for receiving the dosage form.

The flexible wall 4 of the cell 5 comprises an opening 6 small enough to prevent the (non-disintegrated) dosage form 2 from passing through the opening 6. The cell 5 is—via the opening 6—in fluid communication with a further cell 7; both cells are filled with a fluid 8 as a model of chyme or another fluid. The further cell 7 may be implemented as a balloon or a container. Further, the disintegration unit 1a comprises a pressurizable compartment 9, which is defined by the chamber 3 and the flexible wall 4. The pressurizable compartment 9 comprises a measuring means 10 for measuring the pressure in the pressurizable compartment 9. The measuring means 10 is an optional component in the device 1. A force sensor in cell 5 may be used to measure the force that is directly applied to the dosage forms, e.g. to calibrate the controlling means 1b.

The disintegration unit 1a is operably connected to controlling means 1b, which is designed to quantitatively control the introduction or withdrawal of a gas or a liquid into and out of the pressurizable compartment 9, respectively. With operably connected is meant that an operable connection is present that allows the transport of a gas or a liquid from disintegration unit 1a to controlling means 1b and vice versa. An example of an operable connection is link 11', comprising a guide capable of transporting a gas or liquid, such as a tube, a hose or a pipe. The disintegration unit 1a and the controlling means 1b may also be integrated in one single unit, wherein the presence of a link of an elongated form such as link 11' is not necessary.

The controlling means 1b comprise a pressurizing means for pressurizing and depressurizing the pressurizable compartment 9, the pressurizing means including a plunger 11, a plunger pump 12 and a stepper motor 21 for driving the plunger pump 12. Obviously, also other hydraulic actuators can be applied to pressurize and depressurize the compartment 9 in a controllable manner. Further, other types of actuators can be used to modify the pressure in the compartment 9, e.g. a mechanical actuator or a pneumatic actuator. The controlling means further comprise a computer 13, capable of controlling the stepper motor 21 for driving the plunger pump 12. The computer 13 may be capable of receiving data from the measuring means 10. If a measuring means 10 is present in the device 1, it may be present in the pressurizable compartment 9 as shown in FIG. 1. However, it may also be present in the cell 5 or in the plunger pump 12. It is further noted that instead of applying a plunger pump 12, the pressure in the compartment 9 can be arranged otherwise, e.g. by employing valves and flow meters.

The introduction of a gas or a liquid into the pressurizable compartment 9 results in a deformation of the flexible wall 4 and in a reduction of the volume of the cell 5. Analogously, the withdrawal of a gas or a liquid out of the pressurizable compartment 9 results in a deformation of the flexible wall 4 and in an increase of the volume of the cell 5. The deformation of the flexible wall 4 by the introduction and subsequent withdrawal of a gas or a liquid from the pressurizable compartment 9 defines a cycle. The extreme positions of the wall 4 during a cycle of decreasing the cell volume and increasing the cell volume are termed the first state and the second state of the disintegration unit 1a, respectively. Following these changes in the volume of the cell 5 in a cycle, the chyme flows through the opening out or into the cell, respectively. The direction of the fluid communication wherein fluid is moved from the further cell 7 into the cell is defined as direction A. The direction of the fluid communication wherein fluid is moved from the cell 5 into the further cell 7 is defined as direction B. The directions of the corresponding movements of the plunger pump are indicated as A' and B'.

The wall 4 is usually made of a flexible material, such as a polysiloxane. An advantage of a polysiloxane is that it is transparent, which allows a real time monitoring of the disintegration of a dosage form with optical means such as a camera.

The wall 4 may comprise preformed folding sections 30. An advantage of such sections is that the folding of the wall can be accomplished in an essentially reproducible manner. With an essentially reproducible manner is meant that eventual variations in the manner of deforming of the wall are insignificant with respect to the accuracy of measuring and/or the accuracy of controlling the fluid flow.

Although the figures show an asymmetric cell, in a practical situation, the cell may be symmetric with respect to a longitudinal axis.

Figure 2A:
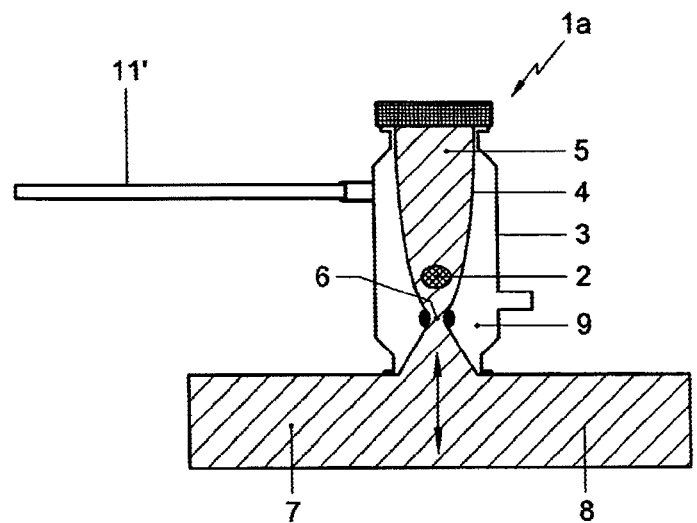
FIG. 2a shows a more detailed schematic side view of a disintegration unit 1a of the device as shown in FIG. 1, wherein the disintegration unit 1a is in the first state.
Figure 2B:
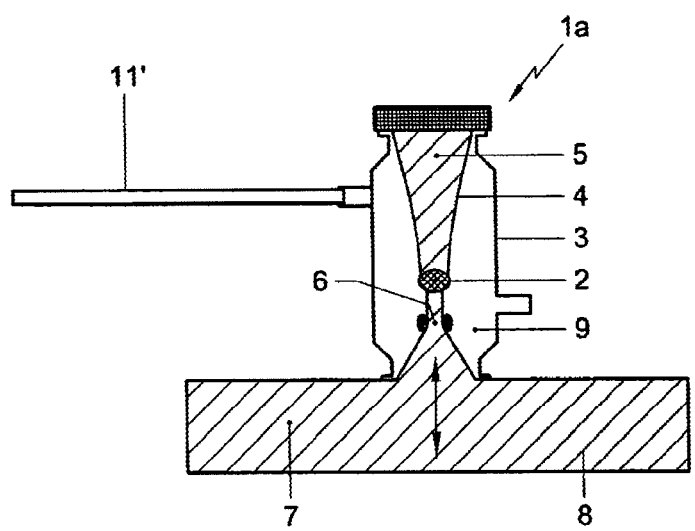
FIG. 2b shows a more detailed schematic side view of disintegration unit 1a of the device as shown in FIG. 1, wherein the disintegration unit 1a is in the second state.

FIGS. 2a-2b each show a more detailed schematic cross sectional view of disintegration unit 1a. FIG. 2a shows the disintegration unit 1a in the first state, the pressurizable compartment 9 being depressurised. FIG. 2b shows disintegration unit 1a in the second state, the pressurizable compartment 9 being pressurised. In this respect it is noted that FIG. 1 shows the disintegration unit 1a in an arbitrary position between positions corresponding with the first state and the second state, respectively. The dosage form 2 experiences a smaller squeezing force in the first state than in the second state.

In a device according to the invention, the cell may be in fluid communication with a further cell via an opening in the wall. The further cell may comprise chyme or a model of chyme. FIG. 1, FIG. 2a and FIG. 2b show embodiments of the invention, wherein the cell comprises an opening 6.

FIGS. 3a-3f each show a cross-sectional view of a wall part 4' of a device 1 according to the invention, the cross-sectional view being taken along the fluid communication directions A,B towards the aperture 6.

It is a disadvantage of a conventional device that a dosage form to be assessed often readily moves to subsequently different locations when it is subjected to a fluid-flow. This makes it difficult to monitor the disintegration of the dosage form, especially when use is made of electronic equipment that is focussed on a specific location of the disintegration device. Further, disintegration of a dosage form at other (non-predetermined) locations makes it difficult to control the conditions wherein the disintegration takes place, and leads to poor reproducibility of the measurements. This problem can be solved by capturing the dosage form in a flexible net, which keeps the dosage form on (or close to) an intended position and allows smaller fragmented components of the dosage form to dissipate with the flow.

In an embodiment, a device according to the invention comprises an opening 6 that is arranged for blocking the dosage form to flow to the further cell. In particular, the opening 6 is arranged for blocking the dosage form and at least the main fragment(s) thereof formed during disintegration to flow to the further volume. The opening may for example comprise one or more items selected from the group of net, bar and sieve.

An advantage of a device according to the invention comprising an opening that is arranged for blocking the dosage form to flow to the further volume, is that the dosage form—or at least the main fragment(s) thereof formed during disintegration—is prevented from flowing with the chyme from the cell 5 into the further cell 7. It is further an advantage that in this way the use of a flexible net can be circumvented.

In case a device according to the invention comprises an opening 6, such opening is usually smaller than the dosage form of which the disintegration is to be assessed, in the sense that at least the longest dimension of the dosage form is longer than the longest dimension of the cross-sectional view of the opening 6 perpendicular to the fluid communication direction, or in the sense that at least the smallest dimension of the dosage form is longer than the smallest dimension of the cross-sectional view of the opening 6 perpendicular to the fluid communication direction.

Figure 3C:
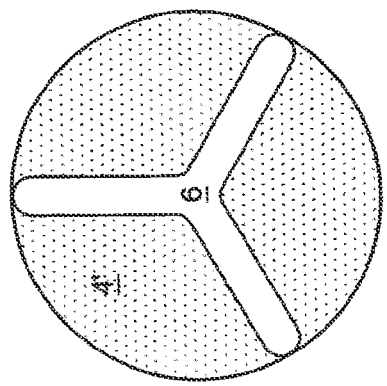
FIG. 3c shows a cross-sectional view of a wall part of a further device according to the invention.
Figure 3F:
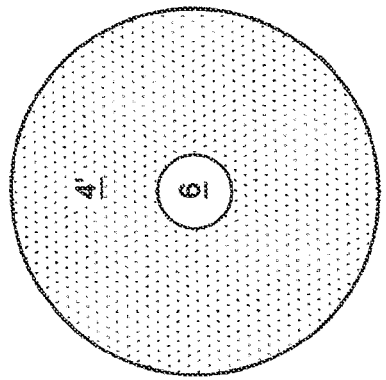
FIG. 3f shows a cross-sectional view of a wall part of a further device according to the invention.
Figure 3B:
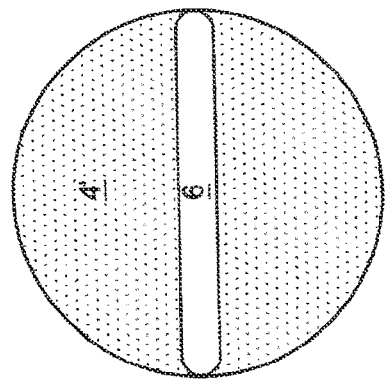
FIG. 3b shows a cross-sectional view of a wall part of a further device according to the invention.

In a preferred embodiment, the opening 6 is slit-shaped perpendicular to the fluid communication direction. Such an opening is e.g. an opening as shown in FIGS. 3a-3e. A slit-shaped opening may have a plurality of radially extending legs that are circumferentially distributed in a substantially uniform manner, for example two radially extending legs (FIGS. 3a-3b), three radially extending (FIG. 3c) or four radially extending legs (FIG. 3d). In a specific embodiment, opening 6 may be disc-shaped oriented in a plane perpendicular to the fluid communication directions A, B (FIG. 3f).

Figure 3E:
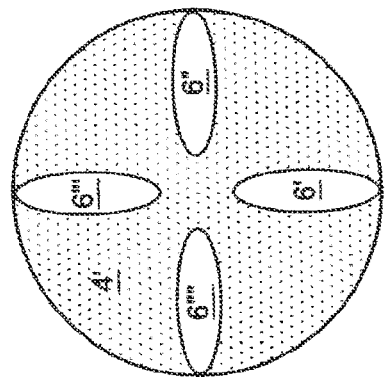
FIG. 3e shows a cross-sectional view of a wall part of a further device according to the invention.
Figure 3A:
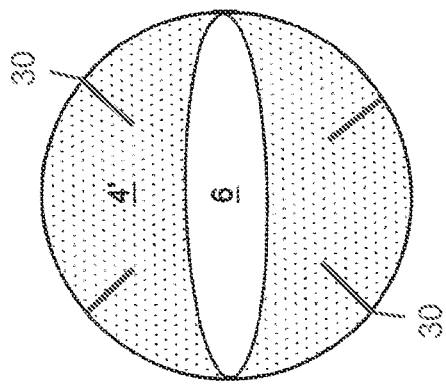
FIG. 3a shows a cross-sectional view of a wall part of a device according to the invention.
Figure 3D:
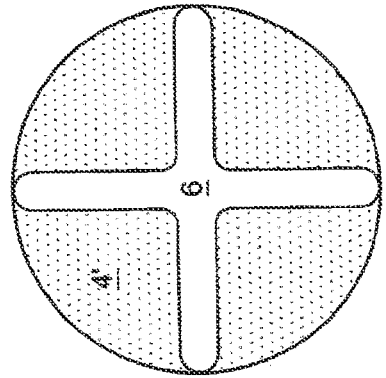
FIG. 3d shows a cross-sectional view of a wall part of a further device according to the invention.

In another embodiment, the cell may comprise a plurality of openings, in particular a plurality of slit-shaped openings, more in particular a plurality of radially extending slit-shaped openings, even more in particular a plurality of radially extending slit-shaped openings that are circumferentially distributed in a substantially uniform manner (FIG. 3e).

In a preferred embodiment, the flexible wall 3 has the shape of a cylindrical sleeve or tube having one open end with an approximately annular opening, wherein the open end has been squeezed into the form of an opening 6, in particular an opening 6 as shown in any of the FIGS. 3a-3f. In a cell comprising such walls, the diameter of the wall contour, in a cross sectional view, gradually reduces when moving towards the opening 6. When the area of the cell, in a cross sectional view, gradually reduces, a dosage form present in the cell remains substantially at the same position with respect to the flexible walls, which allows reproducible pressurisation.

In an embodiment, the opening 6 (or a plurality of openings 6, if present) may be adjustable. In particular, if the opening 6 is an opening that has been created by squeezing an approximately annular opening, the adjustment can be performed in an easy manner by further squeezing the opening or by at least partly releasing the squeezing force on the opening.

The introduction and withdrawal of a gas or a liquid by the controlling means 1b can be controlled quantitatively in terms of the flowrate and the amount of the gas or liquid being introduced. As the flowrate of the gas or liquid can be controlled independently from its amount, it is possible to independently control the duration and the amplitude of a cycle. This is an important advantage of the invention. For example, when introducing and withdrawing a relatively small amount of gas or liquid, one has the choice of doing so with a high or low speed. This results in subsequent cycles with a relatively low amplitude, and with either a short or long duration, respectively. In another way, when introducing and withdrawing the gas or liquid with a relatively low speed, one has the choice of doing so with a small or large amount of the gas or liquid. This then results in subsequent cycles of long duration with either a high or a low amplitude, respectively. It is noted that in this context high speed means that the transition from the first state to the second state is performed relatively fast.

It follows from the above that the amplitude of a cycle is determined by the difference between the deformation of the wall in the first and the second state of that cycle; the largest amplitude possible is the total range wherein the flexible wall can deform: from complete pressurisation to complete pressurisation of the pressurizable compartment 9. When the amplitude of a cycle is less than the largest amplitude possible with the disintegration unit 1b, there is a choice to perform such a cycle over different ranges of the total range wherein the flexible wall can deform. As the force exerted on the dosage form depends on the force that is applied to the wall 4 when the wall touches the dosage form. Accordingly, it is possible to perform a certain cycle with a specific duration and a specific amplitude in combination with a variety of different ranges of the force exerted on the dosage form.

Thus, this property of a device according to the invention makes it possible to control the frequency, speed and the amplitude of the deformation of the wall 4 independently from the force exerted on the dosage form. As such, controlling the fluid flow may include setting a deformation sequence frequency and speed of the wall and/or setting pressure differences between cycles. As the fluid mechanics are substantially completely determined by the frequency, speed and the amplitude of the deformation, a device according to the invention makes it possible to study the fluid mechanics as a function of the force exerted on the dosage form. This is a great advantage of the invention. Further, apart from quantitatively controlling the fluid flow from and into the cell, a contact force that the wall exerts on the dosage form can be controlled. In addition, the quantitatively controlling process can be dynamical or static, meaning that the control settings can be adjusted or maintained, respectively, over time.

The medium for pressurising and depressurising the pressurizable compartment 9 may be a liquid or a gas. The medium is preferably a liquid, because the relatively low compressability of a liquid as compared to a gas allows a more direct control over the disintegration unit 1a.

The direction of the fluid communication between the two cells may in principle be any direction relative to the direction of gravity. In particular, the direction A makes an angle in the range of 0-90° with respect to the direction of gravity, preferably in the range of 0-30° with respect to the direction of gravity, more preferably in the range of 0-10° with respect to the direction of gravity.

Figure 4:
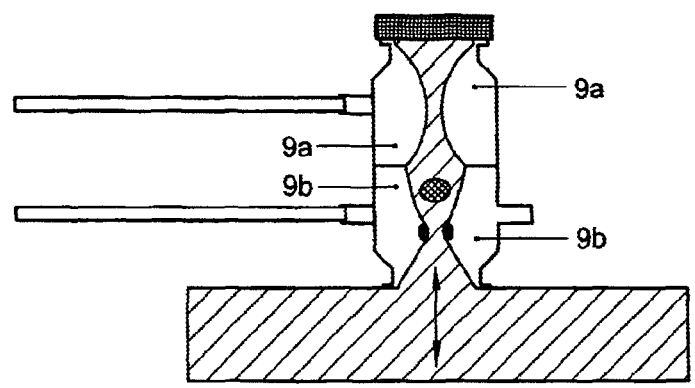
FIG. 4 shows a schematic side view of an embodiment of a device according to the invention comprising a multiple number of pressurizable compartments.

A device according to the invention may comprise a multiple number of pressurizable compartments 9 arranged exterior to the wall for repeatedly deforming the wall between the pressurized state and the depressurized state. An advantage of a multiple number of pressurizable compartments 9 is that the deformation of the flexible wall 4 can be controlled more precisely. Another advantage is that better control can be maintained over the location of the dosage form. FIG. 4 shows an example of a device according to the invention comprising a pressurizable compartments 9a and 9b. Having a multiple number of pressurizable compartments 9, it is for example possible to keep pressurizable compartment 9b relatively depressurised so as to keep the force on the dosage form 2 low, and to induce fluid flow mainly via pressurizable compartment 9a. Such an arrangement makes it possible to even better control the frequency and the amplitude of the deformation of the wall 4 independently from the pressure exerted on the dosage form 2.

A calibration of the device may be performed with respect to the dependency of the volume of the cell on the position of the plunger 11 of plunger pump 12. Such calibration may for example be performed by 1) removing an eventual further cell 7 from opening 6, then 2) bringing the pressurizable compartment 9 into a pressurised state, then 3) bringing the opening 6 of the device into a container filled with a liquid, preferably a measuring jug, such that the opening is below the level of the liquid, i.e. it is in contact with the liquid, then 3) determining for a number of different plunger positions the amount of liquid that has been withdrawn from the container into the cell during depressurising the pressurizable compartment 9. The determination may easily be performed by reading the level of the liquid in the measuring jug.

It is understood that in an alternative method the calibration can comprise filling the cell in a depressurised state with a liquid, and then determining for a number of different plunger positions the amount of liquid that has been released from the cell into the container during pressurising the pressurizable compartment 9.

If the fluid in the pressurizable compartment 9 has a relatively high compressability, such as a gas, calibration of the device may also be performed with respect to the dependency of the pressure in the pressurizable compartment 9 on the position of the plunger 11 of plunger pump 12. Such calibration may for example be performed by determining for a range of plunger positions the pressure in the pressurizable compartment 9. Measuring the pressure can for example be performed with measuring means 10, that may be present in the pressurizable compartment 9 (see also FIG. 1).

Usually, the dependency of the pressure in the pressurizable compartment 9 on the position of the plunger 11 of plunger pump 12 is determined by the type of medium used for pressurising and depressurising. For example, the pressure generated in the pressurizable compartment 9 at a certain plunger position will generally be lower in case a gas is used than in case a liquid is used.

The dependency of the pressure in the pressurizable compartment 9 on the position of the plunger 11 of plunger pump 12 may further be determined by the properties of the flexible wall 4, for example by its rigidity.

Calibration of the device may also be performed with respect to the dependency of the pressure exerted on a dosage form on the pressure that is present in the pressurizable compartment(s). Such calibration may for example be performed by placing a force-meter in the cell 5, in particular on a position in the cell where a dosage form is placed during the assessing of the disintegration.

In an advantageous embodiment according to the invention, the method also includes the step of collecting data being representative of a degree of disintegration of the dosage form, e.g. for analysis purposes.

Further, the invention relates to a computer program for assessing the disintegration of a dosage form in the gastrointestinal tract, the computer program product comprising computer readable code for causing a processor to perform the step of quantitatively controlling a fluid flow from and into a cell surrounded by a wall, and/or quantitatively controlling a contact force that the wall exerts on a dosage form placed in the cell, the wall being repeatedly deformed between a first state and a second state, wherein the volume of the cell in the first state is larger than in the second state.

A computer program product may comprise a set of computer executable instructions stored on a data carrier, such as a CD or a DVD. The set of computer executable instructions, which allow a programmable computer to carry out the method as defined above, may also be available for downloading from a remote server, for example via the Internet.

The method for assessing the disintegration of a dosage form in the gastrointestinal tract can be performed using dedicated hardware structures, such as FPGA and/or ASIC components. Otherwise, the method can also at least partially be performed using a computer program product comprising instructions for causing a processor of the computer system to perform e.g. the step of quantitatively controlling a fluid flow from and into the cell, and/or quantitatively controlling a contact force that the wall exerts on the dosage form.

Figure 5:
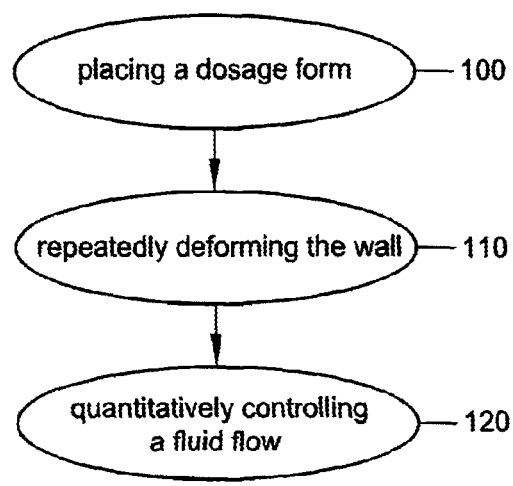
FIG. 5 shows a flow chart of an embodiment of the method according to the invention.

FIG. 5 shows a flow chart of an embodiment of the method according to the invention. The method is used for assessing the disintegration of a dosage form in the gastrointestinal tract. The method comprises the steps of placing (100) a dosage form in a cell filled with a fluid and surrounded by a wall, repeatedly deforming (110) the wall between a first state and a second state, wherein the volume of the cell in the first state is larger than in the second state, by pressurizing and depressurizing, respectively, a pressurizable compartment arranged exterior to the wall; and quantitatively controlling (120) a fluid flow from and into the cell, and/or quantitatively controlling a contact force that the wall exerts on the dosage form.

Figure 6:
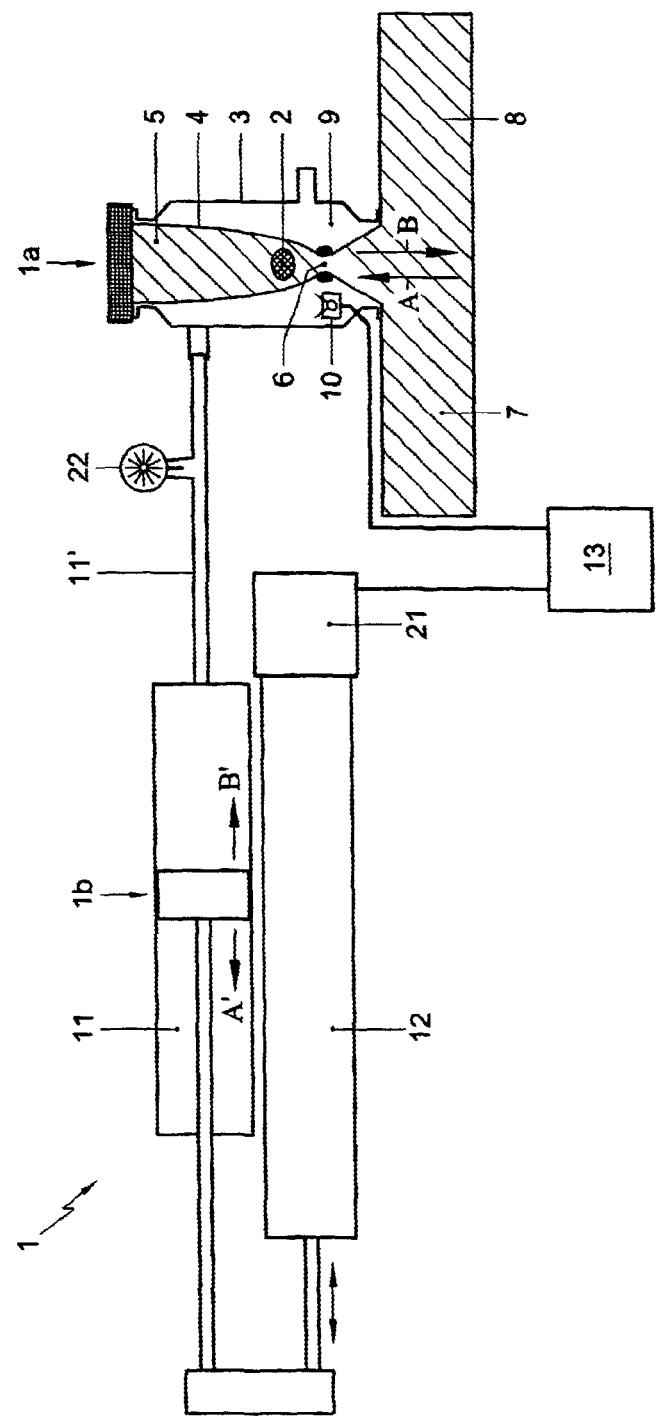
FIG. 6 shows a further embodiment of a device according to the invention.

FIG. 6 shows a further embodiment of a device according to the invention. Here, the device is provided with a pressure controlling unit for ensuring that the pressure in the compartment 9 does not exceed a predetermined maximum level. Thereto, the pressure controlling unit is provided with a pressure sensor 21, such as a manometer, measuring the pressure in the link 11' interconnecting the plunger 11 with the compartment 9. If it is detected to the predetermined maximum pressure level is reached, the pressure can be lowered by sending a signal to the controlling means 1b controlling the pressurizing means such as the plunger 11. Alternatively, the pressure controlling unit may include a local device for depressurizing the link 11' such as a valve. Also, the pressure controlling unit could be provided with an expansion vessel 20, so that a maximum pressure in the compartment 9 can be set.

The invention is not restricted to the embodiments described herein. It will be understood that many variants are possible.

By applying a security system that prevents an overpressure in the pressurizable compartment, it is inherently counteracted that said compartment of the device according to the invention is subjected to an undesirable high internal pressure. Moreover, by selecting a maximum overpressure level, a maximum contact force on the dosage form can be set in a relatively easy way.

It is noted that the device according to the invention can not merely be used for assessing the disintegration of a dosage form in the gastrointestinal tract, but also for studying pathologic, extreme conditions of the gastrointestinal tract.

Other such variants will be obvious for the person skilled in the art and are considered to lie within the scope of the invention as formulated in the following claims.

The invention claimed is:

1. A method for simulating fluid forces on a dosage form in a gastrointestinal tract, comprising the steps of:

placing the dosage form in a cell filled with a fluid and surrounded by a wall;

repeatedly deforming the wall between a first state and a second state, wherein a volume of the cell in the first state is larger than in the second state, by using an actuator for depressurizing and pressurizing, respectively, a pressurizable compartment arranged exterior to the wall; and quantitatively controlling a contact force that the wall exerts on the dosage form by controlling the depressurizing and pressurizing with the actuator, based on data received from a pressure or force sensor disposed in the pressurizable compartment, the data being representative of a measured pressure within the pressurizable compartment.

2. A method according to claim 1, wherein controlling the depressurizing and pressurizing with the actuator includes setting a deformation sequence frequency of the wall, a deformation speed of the wall or a pressure difference between pressures in the pressurizable compartment, corresponding to the first and second state, respectively.

3. A method according to claim 1, wherein controlling the depressurizing and pressurizing with the actuator is performed by adjusting frequency, speed, or amplitude of deformation of the wall.

4. A method according to claim 1, the data being further representative of the volume of the cell.

5. The method of claim 1, wherein the actuator includes a plunger pump and a stepper motor for driving the plunger pump.

6. The method of claim 1, further comprising providing fluid communication between the cell and a further cell via an opening in the wall, while blocking a flow of the dosage form to the further cell.

7. A device for simulating fluid forces on a dosage form in a gastrointestinal tract, comprising a wall surrounding a cell for receiving the dosage form, further comprising at least one pressurizable compartment arranged exterior to the wall for repeatedly deforming the wall between a first state and a second state wherein the volume of the cell in the first state is larger than in the second state, wherein the device also comprises a hydraulic actuator for controlling pressure in the at least one pressurizable compartment to quantitatively control a contact force that the wall exerts on the dosage form by controlling depressurizing and pressurizing between the first state and the second state, based on data received from a pressure or force sensor disposed in the pressurizable compartment, the data being representative of a measured pressure within the pressurizable compartment.

8. A device according to claim 7, wherein the hydraulic actuator comprises a plunger pump and a stepper motor for driving the plunger pump for pressurizing and depressurizing the at least one pressurizable compartment.

9. A device according to claim 7, wherein the wall forms a pocket mainly enclosing the cell for receiving the dosage form.

10. A device according to claim 7, wherein the opening is slit-shaped.

11. A device according to claim 7, wherein the opening has radially extending legs that are circumferentially distributed in a substantially uniform manner.

12. A device according to claim 7, comprising one or more further pressurizable compartments arranged exterior to the wall for repeatedly deforming the wall between the first state and the second state.

13. The device of claim 7, further comprising a further cell in fluid communication with the cell via an opening in the wall, wherein the opening is configured to block a flow of the dosage form to the further cell.

14. A computer program product for simulating fluid forces on a dosage form in a gastrointestinal tract by using a device comprising a cell filled with a fluid and surrounded by a wall, and further comprising a pressurizable compartment arranged exterior to the wall, the computer program product comprising a non-transitory computer readable medium having a computer readable code embodied thereon, the computer readable code including instructions for causing a processor to perform a step of quantitatively controlling a contact force that the wall exerts on the dosage form by controlling depressurizing and pressurizing of the pressurizable compartment using a hydraulic actuator, based on data received from a pressure or force sensor disposed in the pressurizable compartment, the data being representative of a measured pressure within the pressurizable compartment.

15. The computer program product of claim 14, wherein the device further comprises a further cell in fluid communication with the cell via an opening in the wall, wherein the opening is configured to block a flow of the dosage form to the further cell.

\* \* \* \* \*